(12) United States Patent
Schur

(10) Patent No.: US 7,641,645 B2
(45) Date of Patent: Jan. 5, 2010

(54) COMBINATION THROMBOLYTIC INFUSION CATHETER AND DILATOR SYSTEM

(75) Inventor: Israel Schur, Englewood, NJ (US)

(73) Assignee: Angio Dynamics, Inc., Queensbury, NY (US)

(*) Notice: Subject to any disclaimer, the term of this patent is extended or adjusted under 35 U.S.C. 154(b) by 685 days.

(21) Appl. No.: 11/023,901

(22) Filed: Dec. 28, 2004

(65) Prior Publication Data

US 2005/0113800 A1  May 26, 2005

Related U.S. Application Data

(62) Division of application No. 10/348,991, filed on Jan. 22, 2003.

(60) Provisional application No. 60/427,603, filed on Nov. 19, 2002.

(51) Int. Cl.
*A61M 31/00* (2006.01)

(52) U.S. Cl. .................. 604/510; 604/93.01

(58) Field of Classification Search .......... 604/500, 604/506–510, 96.01, 104, 93.01, 164.1, 164.13; 606/194

See application file for complete search history.

(56) References Cited

U.S. PATENT DOCUMENTS

| | | |
|---|---|---|
| 3,888,249 A | 6/1975 | Spencer |
| 4,014,333 A | 3/1977 | McIntyre |
| 4,696,304 A | 9/1987 | Chin |
| 5,021,044 A | 6/1991 | Sharkawy |
| 5,053,004 A | 10/1991 | Markel et al. |
| 5,250,034 A | 10/1993 | Appling et al. |
| 5,267,979 A | 12/1993 | Appling et al. |
| 5,425,723 A | 6/1995 | Wang |
| 5,499,975 A * | 3/1996 | Cope et al. ............ 604/164.1 |
| 5,624,413 A | 4/1997 | Markel et al. |

(Continued)

FOREIGN PATENT DOCUMENTS

EP  0 406 901  1/1991

(Continued)

OTHER PUBLICATIONS

Journal of Vascular and Interventional Radiology, Sep.-Oct. 1997, vol. 8, No. 5, pp. 825-829 Cynamon, et al. "Hemodialysis Graft Declotting: Description of the "Lyse and Wait" Technique".

*Primary Examiner*—Kevin C Sirmons
*Assistant Examiner*—Catherine N Witczak
(74) *Attorney, Agent, or Firm*—Tara L. Custer

(57) ABSTRACT

The present systems combines a drug delivery catheter and a dilator apparatus for use in lysing of clots wherein an internal dilator has a central lumen and an outer catheter is arranged coaxially about said internal dilator. An annular space for fluid passage is sealingly formed between an outer wall of the internal dilator and an inner wall of the outer infusion catheter. Apertures are located in the outer wall of the outer catheter for distributing fluid from the annular space. The internal dilator has a tip element and the outer catheter has an end opening so that together the end opening is occluded by the tip element which protrudes beyond the outer catheter when the outer catheter is arranged coaxially about the internal dilator and additionally the internal dilator is removable from the outer catheter to enable the introduction of a larger guide wire for further medical procedures.

13 Claims, 7 Drawing Sheets

U.S. PATENT DOCUMENTS

| | | |
|---|---|---|
| 5,772,629 A | 6/1998 | Kaplan |
| 5,800,408 A | 9/1998 | Strauss et al. |
| 5,935,108 A * | 8/1999 | Katoh et al. ........... 604/164.11 |
| 6,146,396 A * | 11/2000 | Konya et al. ................ 606/159 |
| 6,245,045 B1 | 6/2001 | Stratienko |
| 6,295,990 B1 * | 10/2001 | Lewis et al. ................. 128/898 |

FOREIGN PATENT DOCUMENTS

| WO | WO 02/055146 | 7/2002 |
|---|---|---|

* cited by examiner ered, and method used for drug delivery.
COMBINATION THROMBOLYTIC INFUSION CATHETER AND DILATOR SYSTEM This application is a divisional of U.S. patent application Ser. No. 10/348,991, filed Jan. 22, 2003, which claims priority under 35 U.S.C. §119 (e) to U.S. provisional application 60/427,603, filed Nov. 19, 2002, the disclosures of which are hereby incorporated by reference.

FIELD OF THE INVENTION

The present invention relates to a medical device apparatus and method for infusion therapy. More particularly, the present invention relates to a coaxial infusion catheter device and method for use in dissolving blood clots.

BACKGROUND OF THE INVENTION

Thrombosis, or blood clot formation, is the most common cause of hemodialysis access graft failure. Graft thrombosis usually results from venous flow obstruction, or stenosis. The location of the stenosis is most commonly found at the graft-vein anastomosis. A narrowing at this area causes a slow down or obstruction of blood flow resulting in the formation of the thrombus within the graft. Venous stenosis is present in over eighty-five percent of clotted grafts. The underlying venous anastamotic stenosis must be corrected in order to avoid recurrence of the thrombus. The venous stenosis is usually treated with balloon angioplasty after the graft has been cleared of the thrombus.

Treatment options for thrombosed grafts include surgical thrombectomy, graft replacement, or percutaneous endovascular thrombolysis. Percutaneous thrombolysis is the least invasive treatment option and has rapidly become the preferred method of treatment at most institutions. It can be accomplished using mechanical thrombectomy devices that macerate the clot or by using a thrombolytic agent to dissolve the clot. Mechanical thrombectomy devices are expensive and often require capital investment. Thrombolytic agents provide a less expensive treatment option.

Tissue plasminogen activators, also known as TPA, are one of the most commonly used thrombolytic agents for clearing dialysis grafts. The drug is introduced into the clotted graft via an infusion catheter or a needle. TPA has a high affinity and specificity for fibrin, a major component of blood clots. It acts upon the clot by binding to the surface and dissolving it by an enzymatic reaction. Time until clot dissolution is dependent on the length and size of the clot, the amount of drug delivered, and method used for drug delivery.

With the "lyse and wait" technique of thrombolysis, TPA or other thrombolytic agent such as urokinase or retaplase is delivered to the graft by a small gauge needle or an infusion catheter. Manual compression is applied to the graft anastomoses during drug administration to ensure targeted drug delivery is restricted to the graft. The procedure is performed without the aid of fluoroscopic guidance. The therapeutic action of the lytic agent typically takes at least one hour depending on the effective distribution of the lytic agent. After clot dissolution, the patient typically is brought into the angiographic suite for fluoroscopic imaging of the graft to identify and visualize residual venous stenosis. Angioplasty of the stenosed segment can then be performed.

SUMMARY OF THE INVENTION

The "lyse and wait" technique of graft clearance has several advantages over other treatment options. With "lyse and wait", the overall procedure time is shortened, the AngioSuite time is minimized, the costs associated with expensive mechanical thrombolysis devices is eliminated and the success rate for clearance is relatively high. Despite these advantages, the traditional "lyse and wait" technique has several potential problems which prevent these advantages from being widely accepted in practice.

When a needle, catheter, or other end hole device is used, non-uniform distribution of the lytic agent across the clot occurs. Therapeutic drug delivery using an end hole device results in concentrated lytic action at the location in the graft where the tip is positioned and insufficient lytic action at locations distant from the tip. This non-uniform drug delivery can result in incomplete thrombus resolution, reduced flow rates, and potential clot migration downstream. In addition, the non-uniform drug delivery results in a longer clot dissolution time period, potentially several hours in duration. Accordingly, there exists a need to provide a uniform distribution of the lytic agent across the entire clot without the use of fluoroscopy.

Furthermore, when an end hole infusion catheter is used as the drug delivery device, the drug must be slowly infused to prevent concentrated jet action through the end hole. Not only does this jet action concentrate the lytic agent in a single location, but it also may cause clot fragmentation and subsequent migration. To avoid high pressure localized delivery and the potential complications, the drug is delivered using a slow infusion method which typically takes three to five minutes with adequate clot dissolution taking up to several hours. Accordingly, there exists a need for an infusion catheter assembly which can a deliver lytic agent quickly and uniformly across the clot without causing a potentially harmful jet action.

To retain the lysing agent within the graft when an end hole catheter or needle is used, the ends of the graft are radially compressed during the injection period. The infusion of the lytic agent through an end hole catheter or angiocath needle is administered slowly over a 3-5 minute period. Compression is required during this infusion time period to ensure that the concentrated drug bolus remains within the graft. Without compression, distribution of the drug to non-targeted areas outside the graft is possible. Providing a infusion catheter device which does not require manual compression during drug injection would allow physicians to quickly and efficiently administer the drug without the assistance of additional medical personnel.

To overcome the non-uniform distribution of the lytic agent, a standard infusion catheter is sometimes used. The catheter is designed with either side holes or slits located along a specified segment of the catheter shaft. The drug exits these side holes equally along the entire length of the clot. Injections using a side hole catheter can be accomplished in one bolus action in three to five seconds rather than over a five-minute period as with an end-hole catheter. Typical drug dwell time within the graft is much less than with an end hole catheter due to uniform and more complete distribution of lytic agent.

Although it provides uniform drug delivery, the infusion catheter technique requires the use of multiple components. In order to access the graft, a needle, guidewire and micropuncture sheath introducer with dilator are required. After the sheath/dilator is removed, an infusion catheter is inserted over the guidewire and into the graft. These additional components not only add to the cost of the device but also add time to the procedure.

In summary, there exists a need for a thrombolytic device that can be percutaneously placed in an outpatient procedural room setting without the use of fluoroscopic guidance. The insertion device should create a minimal puncture. In a preferred embodiment, the device should be able to go over a 0.018" guidewire and provide uniform delivery of the thrombolytic agent without requiring manual compression of graft ends. The procedure should minimize catheter exchanges during a declotting procedure by using a micropuncture catheter as both an access device and an infusion device. The device should allow for the exchange to a 0.035" guidewire and associated procedural components so as to eliminate the need for multiple dilation steps. In addition, the product should be simple to use and inexpensive to manufacture which further improves the business method aspects of the present invention.

Disclosed is an improved infusion catheter device and method for de-clotting procedures. Specifically, a medical device kit is disclosed comprised of components to access the graft, rapidly deliver the therapeutic agent in a uniform distribution pattern across the entire clot, or in a concentrated pattern, and to maintain graft access in preparation for stenosis treatment using angioplasty. By combining components needed for micro-access with a novel infusion catheter/dilator assembly, the procedure eliminates the need for exchange of catheters to accommodate the 0.035" wire or other second guide wire which is larger than the first guide wire. By using a micropuncture catheter as both an access device and an infusion device, the present invention eliminates catheter exchanges during the graft-declotting portion of the procedure.

In a preferred embodiment, the system and apparatus is a kit comprised of a micropuncture needle and compatible guide wire and an infusion catheter/dilator assembly.

Initial access to the graft may be established using standard Seldinger technique. A small-gauge standard micropuncture needle, typically 21-gauge, is inserted into the graft. An 0.018" guidewire is then inserted into the graft through the needle lumen and the needle is removed. The infusion catheter/dilator assembly is inserted into the graft over the guidewire. The size and configuration of the catheter/dilator assembly are designed for easy insertion over an 0.018" guidewire without the need for a micro-access sheath/dilator component to pre-dilate the tract. Typically in the present invention the outer diameter of the catheter/dilator assembly is 5 French approximately 0.067 inches and the outer diameter of the internal dilator is 3 French approximately 0.040 inches.

Once the device is positioned within the graft, the lytic agent is infused into the outer catheter using a standard syringe. The drug is preferably delivered through a side port in the catheter in a single bolus. Under low, steady pressure, the fluid advances into the annular space formed between the dilator and catheter. Occlusion of the catheter end hole by the dilator causes the drug to exit from the slits in the wall of the catheter into the clot mass. The drug will not exit from the end hole of the catheter because it is completely occluded by the dilator.

Only a small amount of drug is required because of the efficient delivery distribution. In addition, there is no need to reposition the catheter to ensure drug application to all segments of the clot. Because the side slits are used for drug delivery rather than the catheter end hole, drug delivery is rapid and uniform with no end hole "jet action". Accordingly, there is no need to apply manual compression to the graft anastomoses during drug delivery to ensure uniform and localized drug distribution.

The present invention includes marking bands that show the position and length of the infusion section or region with the slits or small openings for distributing the lysing agent. These slits allow drug injection at a much faster rate. Typically, 5-10 cc of lytic agent can be delivered to the clot within 3-5 seconds. Because of the rapid and efficient distribution of the lytic agent, time to clot dissolution is decreased. Typically, only 20 to 45 minutes is necessary to declot the graft. Therefore, the efficiency and capacity of the whole clinic is improved because more patients can be treated in a shorter period of time within the outpatient area. Procedural time requiring use of the more expensive angio and/or fluoroscopy suites is limited to the angioplasty procedure.

Once the drug is delivered, the dilator is removed and the catheter is capped off using a standard closed connector type component. When ready for the angioplasty procedure, an 0.035" guidewire or other suitable device can be inserted into the graft through the lumen of the infusion catheter component. An additional catheter exchange is not required because the infusion catheter component will accommodate the larger guidewire size. The infusion catheter component can then be removed leaving the 0.035" guidewire in place to maintain site access. Angioplasty can then be performed using the already placed guidewire. Re-establishing access to the graft and use of a separate dilator is not required.

RELATED PRIOR ART

Micro access sets have been available for years and are considered public domain material. Thrombolysis as a therapy for vascular graft clearance has been taught since the late-1970s. Several infusion catheter designs have been patented. These designs focus on the uniform distribution of the therapeutic agent across the entire clot surface.

U.S. Pat. No. 5,425,723, Wang covers an infusion catheter with an infusion segment at its distal end. The device includes an inner and outer tubular body. The inner tubular body is spaced apart from the outer tube to provide an annular passageway for the delivery of fluid. The design provides for a uniform average flow rate of therapeutic fluid along the length of the infusion segment by the positioning of fluid exit holes on both the inner and outer tubes.

Fluid is introduced to the central lumen of the inner catheter. The therapeutic fluid flows distally and also out the inner catheter exit holes into the annular space between the inner and outer catheter. From the annular space, the fluid flows through the outer catheter exit holes and into the vessel. This indirect flow path counterbalances the decreasing pressure gradient at the distal segment of the catheter, providing a more even drug delivery.

Although an annular space exists for fluid flow between the inner and outer catheter components, the device disclosed by Wang differs significantly from the device of the present invention. The Wang catheter design requires the introduction of fluid into the inner catheter lumen and the fluid only indirectly flows into the annular space. In addition, the inner catheter does not perform a dilation function nor does it occlude the end hole of the outer catheter. The inner catheter cannot be removed to allow the introduction of a larger guidewire.

U.S. Pat. No. 5,800,408 Strauss, et al., covers an improvement on the Wang '723 concept of an infusion catheter. Like Wang's patent, the device includes an inner and outer tubular body with annular passageway between the two for fluid delivery. Instead of having a series of equally spaced exit holes on the inner catheter, Strauss et al., provides a distal and proximal set of exit holes on the inner catheter. This configuration forces fluid to flow distally in the annular space from the proximal holes and proximally from the distal holes. This flow configuration provides enhanced uniform distribution patterns. Strauss et al., also discloses a proximal hub mechanism for adjusting the flow path from one lumen to another.

Again, the concept outlined in the patent differs significantly from the concept of the present invention. The flow path adjustment mechanism can be used to divert flow completely to the annular passageway between the two catheter tubes. Strauss et al., teaches this flow pattern as a way of concentrating fluid delivery proximally rather than for achieving equal flow distribution. Like the Wang disclosure, the inner catheter does not perform a dilation function nor does it occlude the end hole of the outer catheter. The inner catheter cannot be removed to allow the introduction of a larger guidewire.

U.S. Pat. No. 5,250,034 Appling, et al., covers a single lumen infusion catheter for introducing therapeutic agents into the body. The distal segment of the catheter includes pressure responsive valves that provide for uniform fluid distribution. Appling et al., teaches the use of this catheter design for high-pressure injection at relatively high velocities. An occluding ball wire occludes the catheter end hole.

While the patent does include the concept of pressure responsive slits for uniform drug delivery, it uses an occluding ball and does not disclose the use of dilator insertion technique. In addition, Appling does not teach the combination of a micro-puncture access set with an infusion catheter specifically for use in outpatient pre-angioplasty graft de-clotting procedures.

U.S. Pat. No. 5,021,044, Sharkawy covers a multi-lumen catheter for delivery of thrombolytic agents to a blood vessel. The catheter has a first inner lumen for receiving a guidewire, and at least one additional lumen for the delivery of drugs. The coaxial catheter design includes an annular space for the fluid path between the inner and outer catheter tubes. A side-arm port is used to direct drug delivery into the catheter through the annular space between the two catheter tubes. Flow passageways are provided on the distal portion of the outer catheter. These passageways increase in cross-sectional area in a distal direction. The difference in cross-sectional areas provides for uniform fluid delivery.

Although Sharkawy teaches a coaxial catheter to direct the drug flow uniformly through side holes in the catheter, the claims focus on maintaining a desired flow pattern to the target site through the use of non-uniform side holes. He does not teach using the inner catheter for dilation nor does he disclose use of the inner catheter to provide an end hole occluding function. The inner catheter cannot be removed to accommodate introduction of a larger guidewire. There is no discussion of micro access or of specific teachings for dialysis graft de-clotting.

U.S. Pat. No. 6,245,045 Stratienko covers a vascular interventional device for introduction over a guidewire with an end hole and side holes for fluid infusion. The catheter hub is designed to accept another device through its lumen (a dilator) and to accept fluid through a side port. The device includes a dilator for insertion into the device which is dimensioned such that it will fit over a guidewire and within the lumen of the catheter.

There are several key differences between this patent and the present invention. The dilator and sheath components of the '045 invention fit snugly together. This fit does not provide sufficient annular space between the components for infusion of fluid. The coaxial lumen is simply too small for infusions. Before a fluid can be introduced, the dilator must be withdrawn from the sheath and another interventional device inserted. In addition, Stratienko's device includes a standard hemostasis sheath. Hemostasis sheaths are intended to accommodate large interventional devices. The micropuncture set design of the present invention on the other hand is intended to minimize the access puncture size. The micro access components, unlike the hemostasis sheath, allow access with minimal trauma and provide a gradual transition path for larger devices.

DESCRIPTION OF REFERENCE NUMERALS

Figure 1:
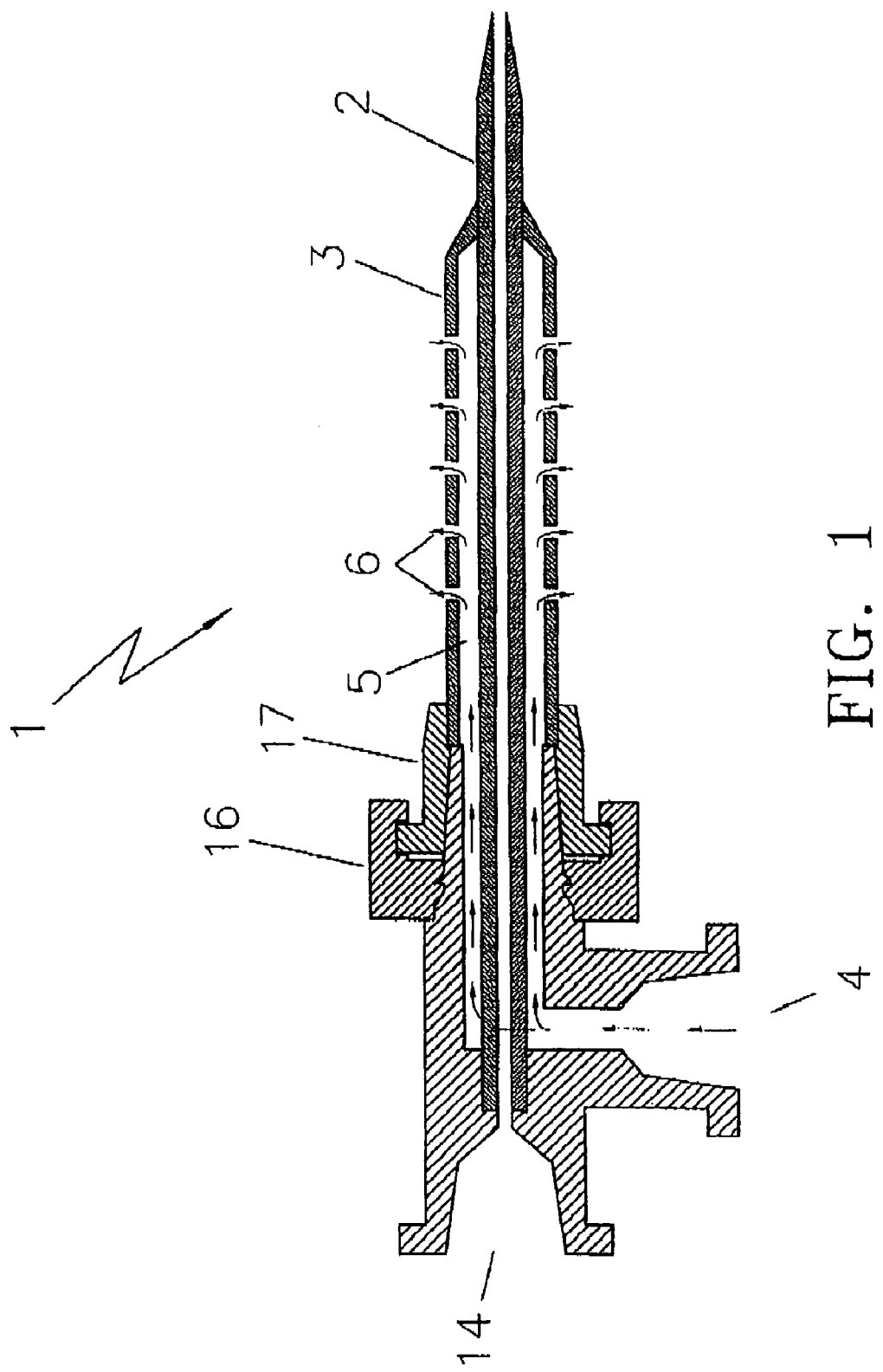
FIG. 1 is a cross-sectional view of the preferred embodiment of the present infusion catheter/dilator system and apparatus.

Turning now descriptively to the drawings, similar reference characters denote similar elements throughout the views. The following numbering is used throughout the various drawing figures:

1 Coaxial infusion catheter system
2 Inner dilator
3 Outer catheter
4 Dilator side port hub
5 Annular fluid passage way
6 Outer catheter side hole slits
7 Distal infusion zone marker
8 Proximal infusion zone marker
9 Dilator shaft
10 Dilator through lumen
11 Dilator hub
12 Dilator distal tip
13 Catheter distal tip
14 Dilator through lumen port
15 Dilator end hole
16 Rotating collar of dilator
17 Outer catheter hub
18 Outer catheter through lumen
19 Infusion zone
20 Positioning marker
21 Outer catheter end hole
22 Graft
23 0.018" guidewire
24 Clot mass
25 Syringe
26 Venous stenosis
27 0.035" guidewire
28 Puncture site

DETAILED DESCRIPTION OF PREFERRED EMBODIMENTS

The present invention can be understood by reference to the FIGS. 1 through 5A-5C. The preferred embodiment of the present invention is based on a coaxial infusion catheter system 1 depicted in FIG. 1. The system is comprised of an internal dilator 2 component shown in FIG. 2 and an outer catheter 3 component shown in FIG. 3. Fluid is infused through a sideport hub 4 into the annular space or annular fluid passageway 5 between the outer wall of dilator 2 and the inner wall of outer catheter 3. For example, a syringe 25 containing the lytic agent can be connected to the sideport hub 4. When injected through the side port 4, the fluid advances through the annular fluid passageway 5 exiting through the side port slits 6 of the outer catheter 3 into the graft.

Figure 3:
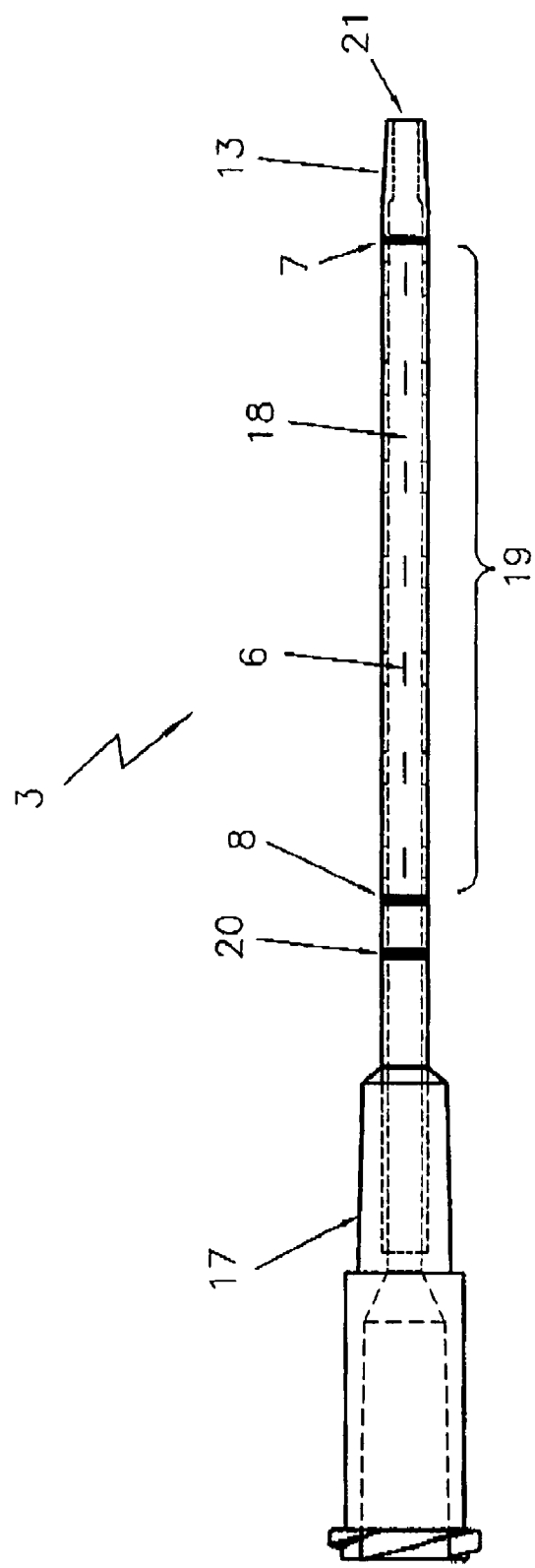
FIG. 3 is a plan view of the outer catheter.

The device components are dimensioned such that the infusion zone 19 (defined as the distance between the distal infusion zone marker 7 and the proximal infusion zone marker 8 in FIG. 3) is maximized and the device length outside the patient is minimized. Specifically, the infusion zone 19 length must correspond to the patient's overall graft or clot mass 24 length (see FIGS. 5A-5C) in order to ensure uniform drug delivery throughout the graft 22. The portion of the device external to the patient is kept as short as possible to avoid complications arising from patient movement during lyse time which is performed in an outpatient waiting room as opposed to a specialized procedure room such as an Angio-Suite or fluoroscopy suite. In addition, the sterile field within an outpatient waiting room setting is restricted. The guidewire, catheter hub and other components external to the patient are intentionally dimensioned to work within restricted or small sterile fields. After the lytic agent is injected, the dilator and guidewire are typically removed and the outer catheter capped off to minimize external component exposure and to maintain the sterile field.

Figure 2:
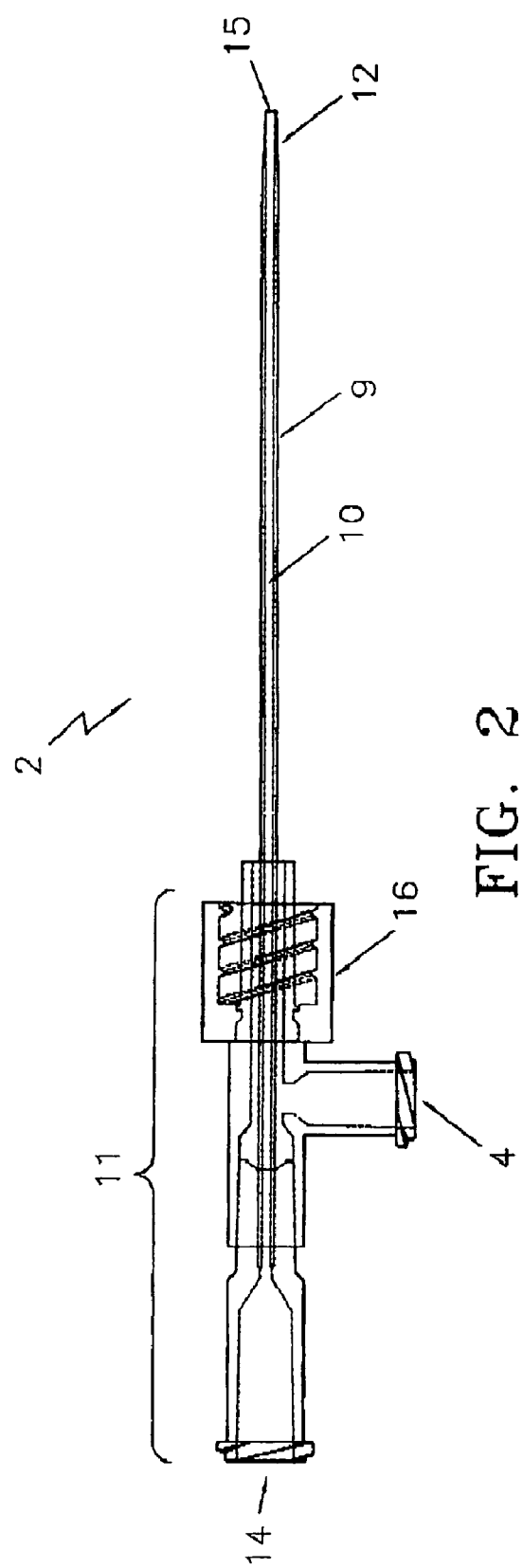
FIG. 2 is a plan view of the inner dilator.
Figure 4:
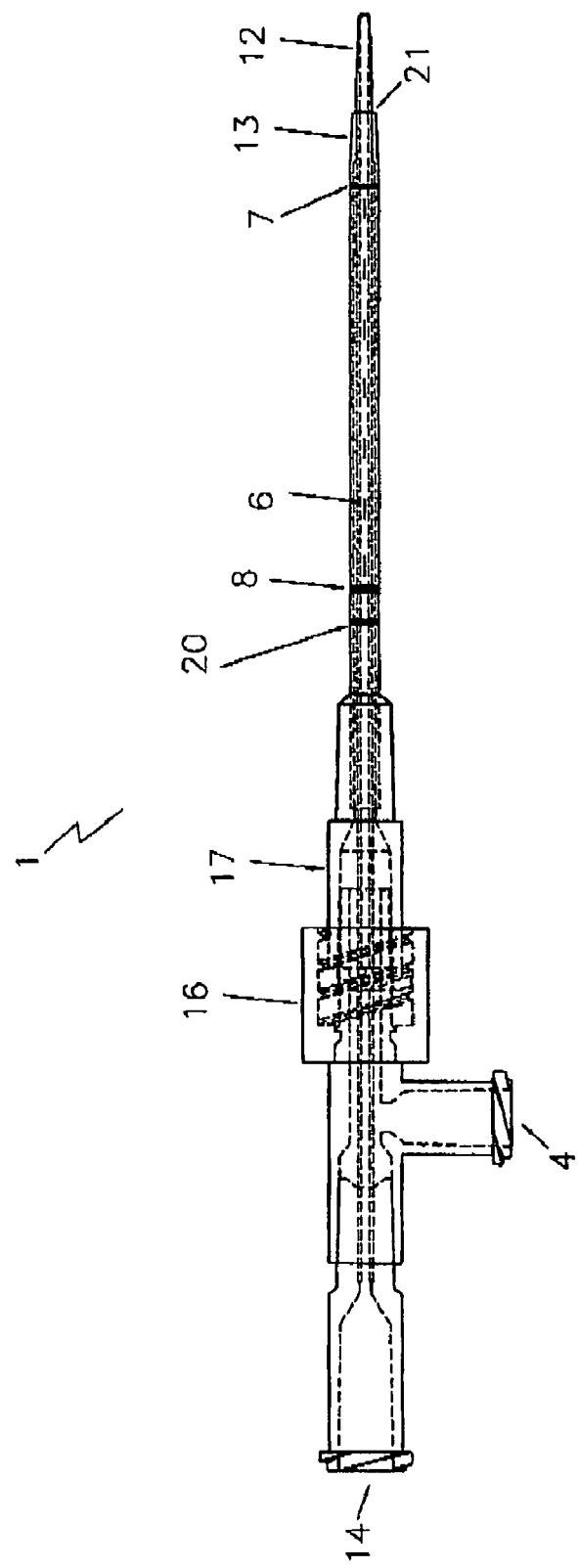
FIG. 4 is a plan view of the preferred embodiment of the infusion catheter/dilator assembly.

In the preferred embodiment, the removable inner dilator 2 of FIG. 2 is comprised of a tubular dilator shaft 9 made of nylon or other similar material and a plastic dilator hub 11. Preferably, the dilator 2 has a 3 French outer diameter with a central lumen 10 that is continuous from the dilator hub 11 to the distal tip end 12 and which accepts a standard 0.018" micro-access guidewire. The dilator tip 12 is tapered to facilitate insertion and dilation of the access track. When assembled with the outer catheter 3 as shown in FIG. 4 the dilator tip 12 extends beyond the catheter distal tip 13 by 1 to 2 cm. The combined dilator tip 12/catheter tip 13 provides an atraumatic profile for gradual access track dilation.

The hub end 11 of the dilator 2 preferably includes two separate infusion ports, a straight through lumen port 14 and a side port 4. Lumen 10 is continuous from the hub port 14 to the distal end of the dilator tip 12 thus providing a direct fluid path from the hub 14 to the end hole 15. Side port 4 is used to inject fluid into the annular space 5 created when the catheter 3 and dilator 2 are assembled together as shown in FIG. 1. Fluid entering through the side port 4 flows into the annular space 5 between the outer wall of the dilator shaft 9 and the inner wall of the outer catheter 3. The hub end 11 of the dilator 2 preferably includes a rotating male luer thread collar 16. When the dilator 2 and catheter 3 are assembled, collar 16 engages the outer catheter hub 17, providing a sealed connection between the two components. The rotating design of the collar 16 allows disengagement of dilator 2 from the outer catheter 3 without causing movement and possible misalignment of the outer catheter 3 within the graft.

Referring now to FIG. 3, the outer infusion catheter 3 has a nylon (or other suitable material) tubular body. In the preferred embodiment, the catheter 3 is of 5 French diameter with a central lumen 18 that is continuous from the proximal to the distal end of the catheter 3. The tubular shaft portion of the catheter 3 includes an infusion zone 19 with a plurality of slits 6, which serve as pressure responsive valves, as described in U.S. Pat. Nos. 5,205,034 and 5,267,979. The pressure responsive slits 6 permit fluid to exit from the catheter lumen 18 in response to a pressure level created by introduction of fluid into the lumen by a syringe. Alternatively, the outer infusion catheter 3 may include a plurality of side holes rather than pressure responsive slits.

As shown in FIG. 3, the infusion zone 19 of the outer catheter 3 is defined as the shaft portion between the distal infusion zone marker 7 and the proximal infusion zone marker 8. Lytic agent injected through the dilator side port 4 into the annular space 5 will exit from the slits 6 on the shaft portion between the two markers 7 and 8 as shown in FIG. 4. Typically, marker 8 is positioned 1 cm proximal to the proximal most pressure responsive slit 6 and marker 7 is positioned on the catheter 3 approximately 1 cm distal to the distal most pressure responsive slit 6. The outer catheter 3 may also have an additional marker, the positioning marker 20. The purpose of positioning marker 20 is to assist the physician in accurately positioning the infusion zone 19 within the graft. Typically, indicator marker 20 is positioned on the catheter 3 shaft about 1 cm proximal to infusion zone marker 8. Positioning marker 20 provides a visual indication of location and depth of the infusion zone 19 segment of the catheter 3, thus ensuring that lytic agent is not infused into a non-target area outside of the graft.

As depicted in FIG. 4, the dilator 2 fits within outer catheter 3 and is sealably connected to the catheter hub 17 by engaging the rotating collar 16. In the preferred embodiment, the outer catheter 3 is a 5 French catheter with an outer diameter of approximately 0.067" and an inner diameter of approximately 0.048". The annular passageway for fluid flow is created between the 3 French dilator and the 5F outer catheter when assembled together. The dimensions of the annular space is sufficient to allow the desired fluid flow into the clot.

The dilator 2 also performs the function of occluding the outer catheter 3 end hole 21 when fully inserted into the catheter lumen 18. The dilator 2 and catheter 3 components are dimensioned such that the dilator 2 fits snugly within and occludes the catheter end hole 21. In the preferred embodiment, the outer diameter of the dilator 2 and the end hole 21 of the outer catheter 3 are both approximately 0.040" thus providing occlusion of the catheter end hole 21. The lumen 18 of the outer catheter 3 is approximately 0.048" in diameter transitioning down to a 0.040" diameter at the outer catheter tip area 13. A separate occluding element such as an occluding ball or wire is not required with the current invention.

The dilator distal tip 12 extends approximately 1-2 cm beyond the distal tip 13 of the outer catheter 3. Tip 12 is tapered to provide a smooth, gradual transition between the 0.018" guidewire diameter and the dilator outer diameter. Similarly, the outer catheter 3 distal tip 13 is also tapered to provide a smooth transition between the dilator 2 and the outer diameter of catheter 3. This transition zone facilitates insertion and dilation of the access track without requiring the use of a separate micropuncture sheath dilator.

The catheter/dilator assembly 1 depicted in FIG. 1 is novel in several aspects. The annular space 5 between the catheter 3 and dilator 2 is large enough to provide a fluid passageway. The pressure responsive valves 6 ensure uniform distribution of the drug. The dilator 2 provides multiple functions including track dilation, which eliminates the need for a separate introducer/sheath dilator as required in the art. The dilator 2 also acts as the occluding mechanism for the catheter end hole 21, eliminating the need for an occluding ball guidewire or other standard end hole occlusion mechanism as required in the art. The dilator 2 accepts up to an 0.025" guidewire, but can be removed to allow the insertion of up to an 0.038" guide wire through the catheter lumen 18, whereby eliminating the need to re-establish access for angioplasty for example. Therefore, the present invention eliminates steps and structures required in the art, allows the patient to be in the outpatient room or clinic receiving lyse and wait therapy to dissolve the clot, which minimizes the time the patient will have to spend in the much more expensive angio suite or fluoroscopy room. Accordingly, the entire clinic is made more efficient from a capacity and business standpoint.

Method of Use

Figure 5A:
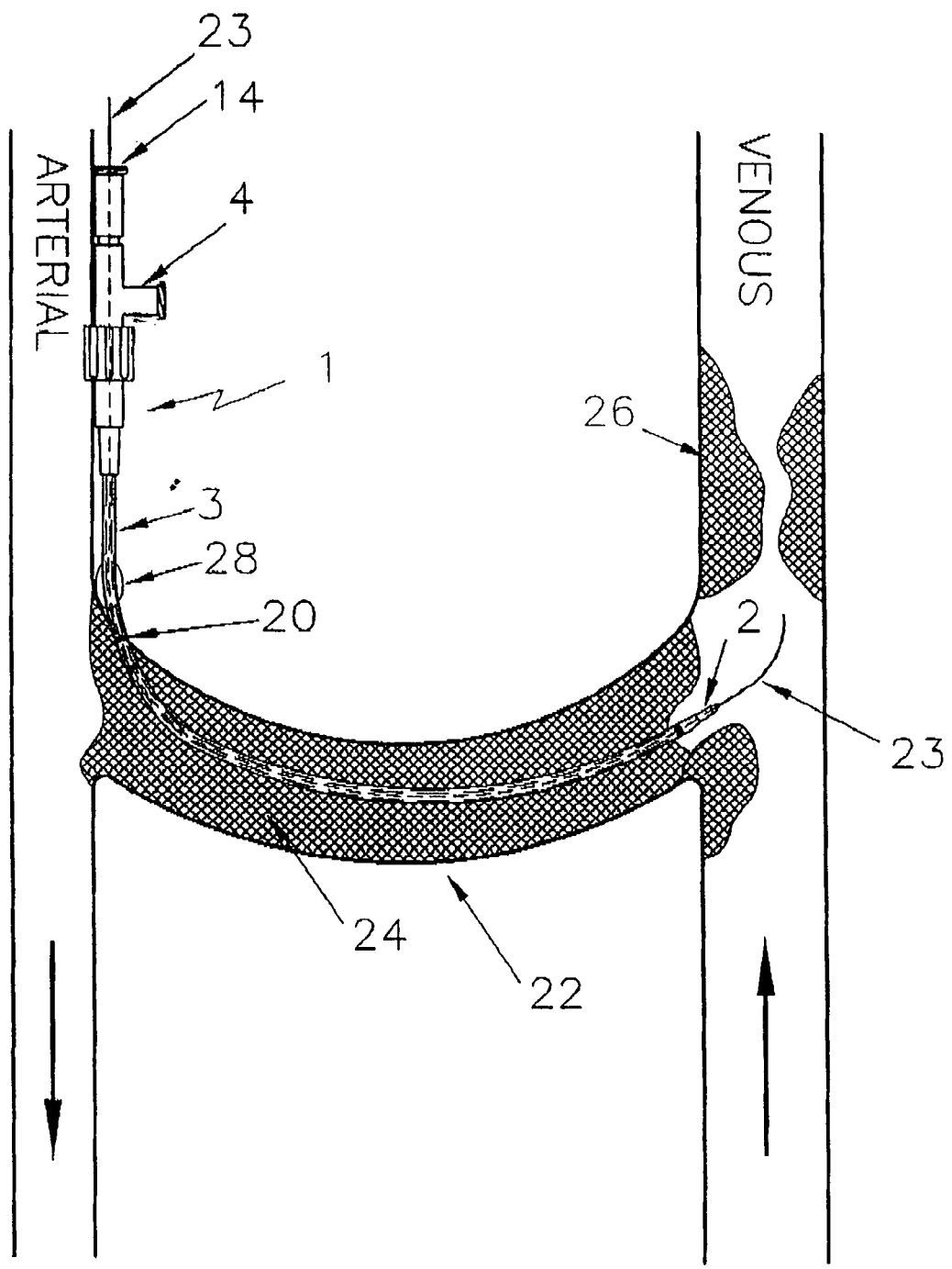
FIG. 5A is a schematic view of the infusion catheter/dilator assembly within a dialysis graft prior to lysing treatment.
Figure 5B:
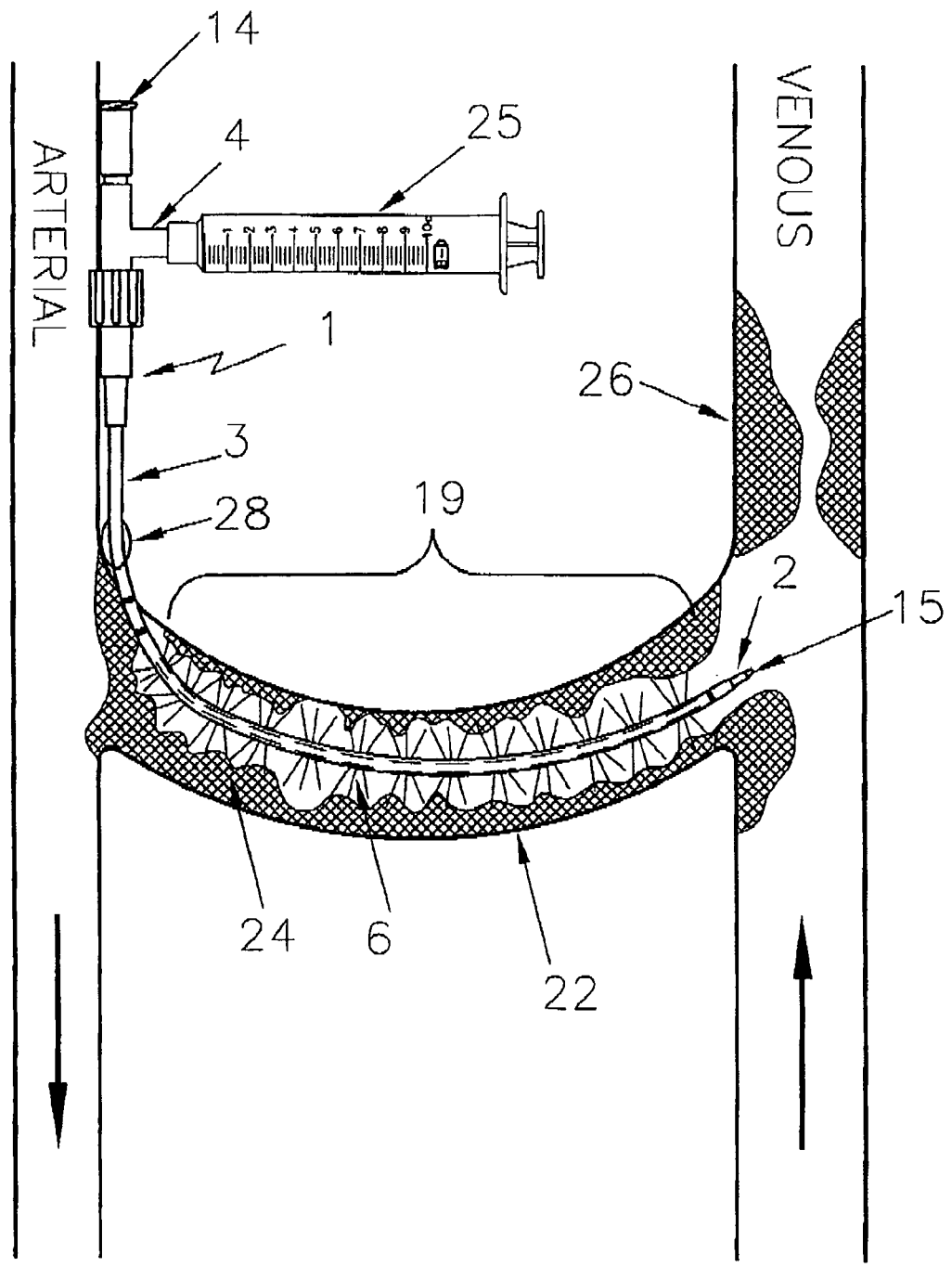
FIG. 5B is a schematic view of the infusion catheter/dilator assembly within a dialysis graft during the lysing procedure.
Figure 5C:
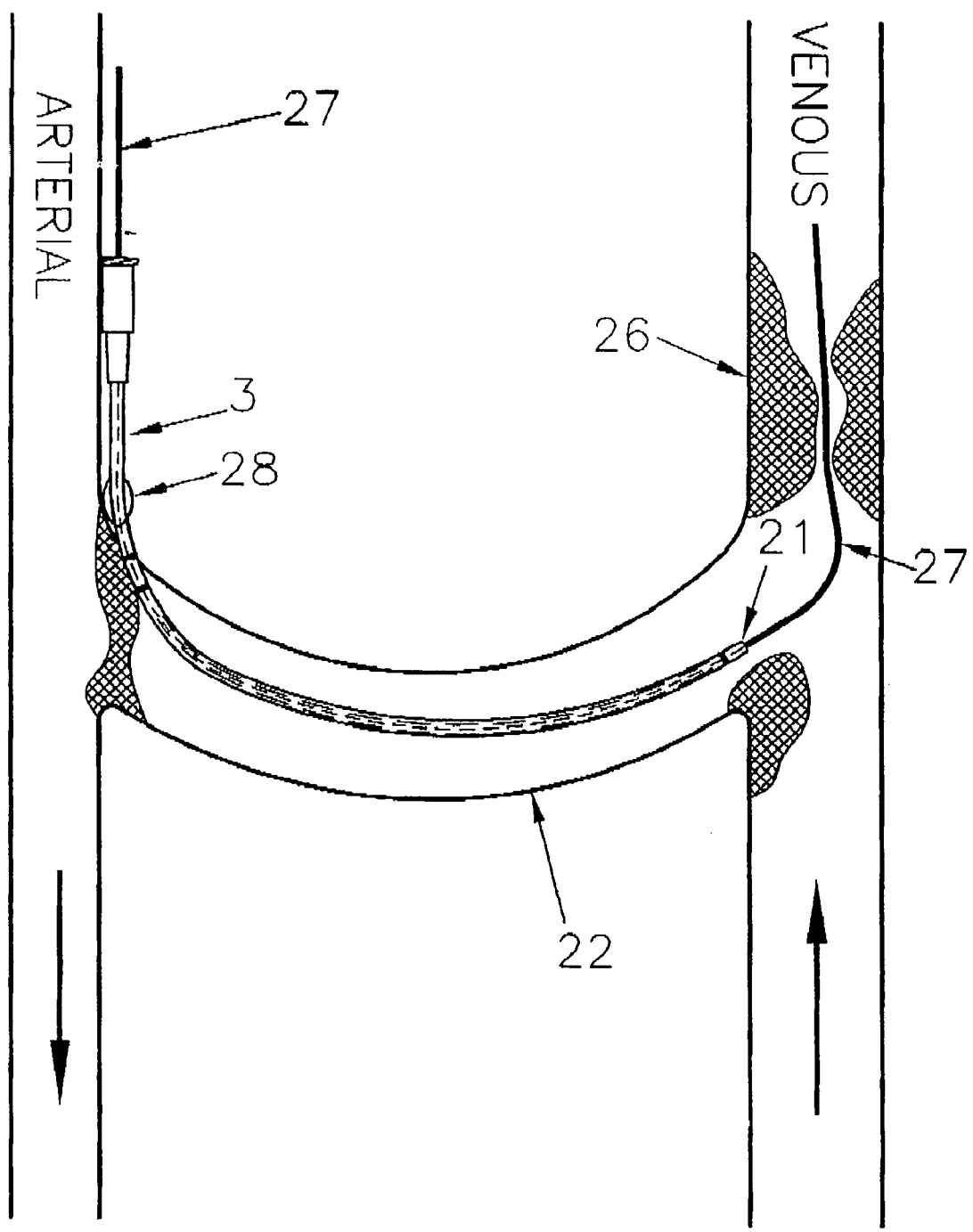
FIG. 5C is a schematic view of the infusion catheter within the dialysis graft after undergoing lysing showing the clot cleared.

The method of use of the current invention is described in reference to FIGS. 5A through 5C. While in the outpatient area, a micropuncture needle (not shown) is used to puncture the skin adjacent to the graft at puncture site 28. The needle is inserted into the graft 22 pointing in the direction of the venous anastomosis. An 0.018" guidewire 23 is inserted through the needle and into the graft 22. After the needle is removed, the dilator/catheter assembly 1 of the current invention is introduced into the graft 22 by advancing the assembly 1 over the guidewire 23. The catheter/dilator assembly 1 is advanced as a unit into the graft 22 until positioned within the clot mass 24 as shown in FIG. 5A. The positioning marker 20 is used as a visual indicator of the overall position of the infusion zone 19, thus providing the physician with confirmation that the infusion zone 19 is completely within the occluded graft 22 as shown in FIG. 5B.

While still in the outpatient clinic area, a syringe 25 containing the lytic agent is connected to the side port hub 4 of the catheter/dilator assembly 1. The lytic agent is injected through the annular passageway 5 between the inner dilator 2 and outer catheter 3 (FIG. 1) and exits from the plurality of slits 6 into the clot mass 24 as depicted in FIG. 5B. Typically, between 5 and 10 cc of lytic agent is injected uniformly into the clot mass 24 over a period of 3-5 seconds. Manual compression of the arterial and venous ends of the graft 22 is not required due to the targeted distribution of the lytic agent which is restricted to the clotted 25 area. The 0.018" guidewire 23 may remain in place within the lumen 10 of the dilator 2 or may be removed, based on the physician's preference. The patient remains in the outpatient clinic area while the lytic agent dissolves the clot mass 24. Due to the uniform distribution of the drug across the entire clot mass 24, lysing time may be a short as 20 minutes.

When lysis is complete, the patient is brought into the fluoroscopic or angiographic suite for an angiogram of the graft 22. Injection of contrast media can be administered directly through the dilator/infusion catheter system 1. Typically, dilator 2 is removed and contrast media is injected directly into hub 17 of outer catheter 3 exiting from the end hole 21. Alternatively, contrast media is injected through the straight through port 14 into the lumen of the inner dilator and exits out of the dilator end hole 15. Contrast media can also be injected through the side port 4 causing distribution of the fluid through the side holes or slits 6. The angiogram will identify any residual venous stenosis 26.

In preparation for dilation of the venous lesion 26, the 3F dilator 2 is detached and removed from the outer catheter 3. A 0.035" guidewire 27 is then inserted through the lumen 18 of the outer catheter 3 and advanced through the catheter end hole 21 into the venous stenosis 26, as depicted in FIG. 5C. Once guidewire 27 is positioned across the venous stenosis 26, the outer catheter 3 is removed from the cleared graft 22. A high-pressure angioplasty balloon is typically used to dilate the stenosed venous segment 26. The angioplasty balloon can be advanced directly over the already-in-place 0.035" guidewire 27 or can be introduced using a standard sheath assembly.

OTHER EMBODIMENTS

While certain novel features of this invention have been shown and described above, the present invention may be embodied in other specific forms without departing from the spirit or essential characteristics of the invention such as different catheter sizes, materials, and configurations and different guide wire sizes. The described embodiments are to be considered in all respects only as illustrative and not as restrictive. Clearly, the invention also envisions the use of different sized catheters and wires. For example, in the future where still conceptual devices such as nano-technology sized microsurgical robots, and fiber optics for lasers, may be guided over wires and into grafts or other ports to the body. Various omissions, modifications, substitutions and changes in the forms and details of the device illustrated and in its operation can be made by those skilled in the art without departing in any way from the spirit of the present invention.

What is claimed is:

1. A method for an improved thrombolytic lysing technique comprising:
   puncturing a hemodialysis graft with a micropuncture needle;
   inserting a micropuncture guide wire through the micropuncture needle into the hemodialysis graft;
   removing said needle from the hemodialysis graft;
   selectively coupling an internal dilator and a catheter to form a combination dilator and catheter apparatus, wherein the internal dilator and the catheter define an annular space therebetween, and wherein the catheter defines a plurality of apertures in fluid communication with the annular space;
   inserting the combination dilator and catheter apparatus over said guide wire into the hemodialysis graft to a selected position wherein at least one of the plurality of apertures is positioned within a clot;
   infusing a lysing agent into the hemodialysis graft through said combined dilator and catheter apparatus via the annular space and the at least one of the plurality of apertures positioned within the clot to distribute the lysing agent to the clot;
   selectively decoupling the internal dilator from the catheter;
   removing said internal dilator;
   inserting a second larger guide wire into said catheter component of said combined dilator and catheter component; and
   removing said catheter component from the hemodialysis graft while maintaining access via said second larger guide wire for subsequent medical procedures.

2. The method for an improved thrombolytic lysing technique of claim 1 wherein:
   said internal dilator component is dimensioned to accept up to 0.025" diameter first guide wire;
   said catheter component is dimensioned to internally accept up to a 0.038" diameter second guide wire after said internal dilator component is removed.

3. The method for an improved thrombolytic lysing technique of claim 1 wherein:
   said first guide wire has substantially a 0.018" diameter and second larger guide wire has substantially a 0.035" diameter.

4. The method for an improved thrombolytic lysing technique of claim 1 wherein:
   said internal dilator component has an outer diameter of 3 French; and
   said catheter component has an outer diameter of 5 French.

5. The method for an improved thrombolytic lysing technique of claim 1 wherein:
   said catheter component includes marking bands located near said apertures to indicate where a region of said apertures begins and ends in said catheter.

6. The method for an improved thrombolytic lysing technique of claim 1 wherein:
   said apertures are uniformly positioned in said outer wall of said outer catheter for uniformly distributing fluid from said annular space.

7. The method for an improved thrombolytic lysing technique of claim 1 wherein:
   said apertures are pressure actuated recloseable exit slits normally biased in a closed position for uniformly distributing fluid in response to pressure.

8. The method for an improved thrombolytic lysing technique of claim 1 wherein:
   said apertures are small open orifices.

9. The method for an improved thrombolytic lysing technique of claim 1 wherein:
   said internal dilator has a distal tip adapted for dilation; and
   said distal tip extends up to 2 cm beyond said outer catheter's occluded distal end.

10. A method for enhancing declotting clinic capabilities to minimize patient time and costs incurred in using specialized procedure rooms associated with thrombolytic declotting procedures comprising:
    performing on a patient located outside of the specialized procedure rooms the steps of:
    puncturing a graft with a micropuncture needle,
    inserting a micropuncture guide wire into the graft through the micropuncture needle;
    removing said micropuncture needle from the hemodialysis graft;
    selectively coupling an internal dilator and a catheter to form a combination dilator and catheter apparatus, wherein the internal dilator and the catheter define an annular space therebetween, and wherein the catheter defines a plurality of apertures in fluid communication with the annular space;
    inserting the combined dilator and catheter apparatus over said guide wire into the hemodialysis graft to a selected position wherein at least one of the plurality of apertures is positioned within a clot;
    infusing a lysing agent into the hemodialysis graft through said combined dilator and catheter apparatus via the annular space and the at least one of the plurality of apertures positioned within the clot to distribute lysing agent to a clot;
    removing the internal dilator;
    removing said micropuncture guide wire; and
    inserting a second larger guide wire therethrough the catheter to maintain graft access in preparation for further medical procedures.

11. The method of claim 10 wherein:
    said micropuncture guide wire has substantially 0.018" diameter and a second larger guide wire has substantially a 0.035" diameter.

12. The method of claim 10 wherein the further medical procedure is declotting of veins or arteries.

13. The method of claim 10 wherein the further medical procedure is angioplasty.

* * * * *